US009861511B2

(12) United States Patent
Torres-Leon (10) Patent No.: US 9,861,511 B2
(45) Date of Patent: Jan. 9, 2018

(54) DRAINAGE BAG SUPPORT APPARATUS (71) Applicant: Global Medical Innovations, LLC, Woburn, MA (US)

(72) Inventor: Mario Torres-Leon, Woburn, MA (US)

(73) Assignee: Global Medical Innovations, LLC

( * ) Notice: Subject to any disclaimer, the term of this patent is extended or adjusted under 35 U.S.C. 154(b) by 380 days.

(21) Appl. No.: 14/150,287

(22) Filed: Jan. 8, 2014

(65) Prior Publication Data
US 2014/0194839 A1 Jul. 10, 2014

Related U.S. Application Data (60) Provisional application No. 61/750,297, filed on Jan. 8, 2013.

(51) Int. Cl.
*A61F 5/44* (2006.01)

(52) U.S. Cl.
CPC .................. *A61F 5/4408* (2013.01)

(58) Field of Classification Search
CPC combination set(s) only.
See application file for complete search history.

(56) References Cited

U.S. PATENT DOCUMENTS

| | | | | |
|---|---|---|---|---|
| 4,122,851 A | * | 10/1978 | Grossner | A61F 5/4408 128/DIG. 15 |
| 4,511,358 A | * | 4/1985 | Johnson, Jr. | A61F 5/4404 224/191 |
| 4,846,816 A | | 7/1989 | Manfredi | |
| 5,004,136 A | * | 4/1991 | Leath | A45F 5/02 224/148.5 |
| 5,053,027 A | * | 10/1991 | Manfredi | A61F 5/455 600/574 |
| 5,087,251 A | | 2/1992 | Heyman et al. | |
| 5,643,236 A | | 7/1997 | Hadley | |
| 6,599,278 B1 | | 7/2003 | Nichols | |
| 6,610,032 B1 | | 8/2003 | Prody | |
| 7,165,706 B2 | | 1/2007 | Barr | |
| D543,025 S | * | 5/2007 | Cicione | D3/224 |
| D588,802 S | * | 3/2009 | Cicione | D3/228 |

(Continued)

OTHER PUBLICATIONS

Catheter Leg Bag Support Belt-Size Large up to 58'waist; Webpage print-out from online merchant (from interne address: http://www.amazon.com/Catheter-Support-Belt-Large-waist/dp/B003219154; printed on Dec. 9, 2013).

*Primary Examiner* — Tatyana Zalukaeva
*Assistant Examiner* — Guy K Townsend (57) ABSTRACT

The present invention relates to a drainage bag support apparatus that has a trunk belt, one or more support straps, and additional means to connect the trunk belt and the support straps together, to adjust the support strap, and to attach a drainage bag. The apparatus of the present invention allows one to adjust and lock the length of the support strap, to change the positions of the trunk belt and the support straps, and to use one or more drainage bags. Methods of using the drainage bag support apparatus include securing the trunk belt around an individual and securing one or more drainage bags to the drainage bag support apparatus. Kits that provide the components of the drainage bag support apparatus to be used along with at least one drainage bag are also described herein.

5 Claims, 4 Drawing Sheets

(56) References Cited

U.S. PATENT DOCUMENTS

| | | |
|---|---|---|
| 7,517,340 B2 * | 4/2009 | Barrientos ................ A61F 5/44 128/876 |
| 7,517,341 B2 | 4/2009 | Barrientos |
| 2008/0140034 A1 | 6/2008 | Edling |
| 2009/0234310 A1 | 9/2009 | Marshall |
| 2011/0202024 A1 | 8/2011 | Cozzens |

* cited by examiner

DRAINAGE BAG SUPPORT APPARATUS

RELATED APPLICATIONS

This application claims the benefit of U.S. Provisional Application No. 61/750,297, filed Jan. 8, 2013.

The entire teachings of the above application are incorporated herein by reference.

BACKGROUND OF THE INVENTION

Placement of drainage catheters is used for a variety of medical conditions each year by millions of patients in the world. The drainage catheters are placed using traditional surgical techniques or using minimally invasive procedures performed by radiologists through the guidance of imaging.

Traditionally, a drainage catheter is connected to a drainage bag that is often hung by the patient's side, pinned to patient's clothing, or strapped to a part of patient's lower extremity such as a thigh or a leg. Traditional positioning of the drainage bag is awkward, limits mobility, and presents additional challenges when patients perform daily tasks (e.g., getting dressed).

A need exists for a device to better secure the drainage bag to the patient during use. A further need exists for a drainage bag support device to be secured to the patient and still allow the patient, while using the drainage bags, to more easily get dressed and perform other daily tasks. Yet a further need exists for a more versatile drainage bag support device that secures the drainage bag to various areas of the patient's trunk (e.g., to the waist and/or thorax) so that various types drainage bags can be secured.

SUMMARY OF THE INVENTION

The present invention relates to an apparatus that allows an individual to support a drainage bag. More particularly, the present invention allows one to support a single drainage bag or multiple bags, to secure the apparatus from a variety of positions which concomitantly allows placement of the bag or bags at a variety of locations on the individual's body.

The present invention includes an apparatus that can be used by an individual who has a medical condition that involves drainage of bodily fluids. The apparatus can be used to support (e.g., hold, carry, or both) a single drainage bag or multiple drainage bags. The apparatus, also referred to as "a drainage bag support apparatus," includes a trunk belt and a (e.g., one or more) support strap. The trunk belt includes a fastener that enables it to be secured around the trunk (e.g., chest, thorax, abdominal and/or waist) of an individual. The support strap is connected to the trunk belt using a (e.g., one or more) slider. The present invention further includes a drainage bag or multiple drainage bags that are connected to the support strap with a (e.g., one or more) retention device. The apparatus embodies various combinations of the foregoing, including multiple sliders, multiple support straps, and multiple retention devices. The slider is able to move or slide along the trunk belt. The support strap has a length that is adjustable. A user can shorten and/or lengthen the effective length of the support strap, the effective length being the distance between its attachment point to the slider and its attachment point to the retention device. The phrase "length of the support strap" also refers to the effective length of the support strap. The support strap can be a strap, suspension strap, band, loop, chain, any combination thereof, and the like. In an embodiment, the support strap is made from non-elastic materials such as nylon, polyester (e.g., polyethylene terephthalate), leather, cotton, wool, polyethylene, or any combination thereof. To accommodate this adjustment of length of the support strap, the retention device is able to slide along the support strap, so as to be repositioned to receive the drainage bag or drainage bags optimally at a lower end of the support strap. In an embodiment, the slider, in addition to attaching to the trunk belt, is able to receive the support strap. In an aspect, a hook can be used to receive support strap. In certain embodiments, the trunk belt can have two ends, and the fastener attaches the first end to the second end. Alternatively, in another embodiment, the trunk belt can attach the first end to a portion of the trunk belt. Certain embodiments include a retention device that receives two or more drainage bags. Examples of a retention device include a quick release clip, a hook, loop, clip, any combination thereof, and the like. In other embodiments, the present invention includes two or more sliders attached to the trunk belt wherein the sliders slide along the trunk belt. Further embodiments of the present invention include a position adjuster at the support strap. The position adjuster allows the user to adjust the effective length of the support strap, making it longer or shorter, and it also allows the user to lock the effective length of the support strap into place. Examples of a position adjuster include a cam buckle, a fastener, snap, buckle, button, hook, clip, hook and loop fastener, any combination thereof, and the like. In additional embodiments, the trunk belt can be a harness, a loop, a band, a rope, or a belt and the like or can be made from an elastic material, such as elastane, latex, rubber, or any combination thereof. The slider can be any device that can attach to the trunk belt at one or more locations along the belt. Alternatively, sliders can include a device that can also be moved along the trunk belt in at least one direction. An exemplary device is a tri-point slider, which has two openings through which the belt is treaded, effectively creating three sections, two on one face, and one on the face. This design of the present invention allowed the tri-point slider to be secured at more than one position along the belt. Other embodiments of the slider include those with a single opening, or a slider with more than two openings, as long as the slider has at least one opening through which the belt or a portion thereof is threaded. In an embodiment, the sliders include additional members, such as a hook member, that enable the slider to connect to the support straps. The sliders can be made of any material, including metals, wood, glass, ceramics, polymers, fabrics, plastics, and the like. In yet another embodiment, the slider can be included as an inherent part of the support strap, which would effectively loop around or through the trunk belt. Examples of the fastener include snaps, buckles, buttons, laces, clips, hook and loop arrangements, magnets, and multiples, combinations, and the like thereof. In an additional aspect, the fastener can also be inherently part of the trunk belt, in which case the trunk belt would be fitted around a trunk of an individual either due to its elastic properties or due to the adjustability of its length before use.

The present invention further relates to an apparatus to be used to support a drainage bag or multiple drainage bags. The apparatus is for use by individuals that have a medical condition in which body fluids is drained. The apparatus includes a trunk belt, a slider, two or more of support straps, a two or more position adjusters, and two or more retention devices. The trunk belt includes a fastener that allows for the trunk belt to be secured around the trunk of an individual. A support strap is connected to the trunk belt with attachment to a slider or to multiple sliders. A support strap has an effective length, which is the distance from the slider to the retention device, when in use. This effective length can be adjusted or changed, for example by use of a position adjuster. A position adjuster, in addition to lengthening or shortening of the effective length of a support strap, can also lock the effective length of a support strap into place. Locking the effective length of a support strap refers to a length that remains substantially the same, for instance by changing less than, for example, about 10%, about 5%, or about 1% of its locked in effective distance during use (e.g., for a period of at least, for example, about 30 minutes, about 1 hour, about 2 hour, or about 24 hours following the locking in of the effective length). In an aspect, the slider, when in use during drainage, is attached to at least two components: a trunk belt and a support strap. In addition, the slider is able to move or slide along the trunk belt; thus, it is slidably attached. This sliding can be minimal, so as to remain substantially stationary when the apparatus is in full use, or can be more substantial, effectively allowing the slider to be repositioned to any point along the trunk belt as the user desires. By the apparatus being in full use, it is meant that the trunk belt is connected to at least one slider, the slider is connected to at least one support strap, the support strap is connected to at least one position adjuster and to at least one retention device, and the retention device is connected to at least one drainage bag. A retention device is able to attach to a drainage bag or to multiple drainage bags and also to a support strap. Alternative embodiments of the apparatus have two or more sliders, instead of just one, slidably attached to the trunk belt. Other embodiments include retention devices that attach to one support strap and also attach to multiple drainage bags. The multiple drainage bags refers to two drainage bags, three drainage bags, four drainage bags, etc. In additional embodiments, the drainage bags have two or more bag openings, and the drainage bags are attached to the apparatus either by the same retention device or different retention devices.

The present invention additionally embodies methods of using a drainage bag support apparatus. Such a drainage bag support apparatus is often used by an individual who has a medical condition in which biological fluids are drained. The fluids are typically drained into drainage bags, which are to be supported with the aid of the drainage bag support apparatus of the present invention, as described herein. A method of using the apparatus described herein includes securing a trunk belt of the apparatus around the thorax or abdominal area of an individual, and connecting one or more drainage bags to be used by the individual to a retention device. The trunk belt can have a fastener for securing the trunk belt around a trunk of an individual. By trunk, it is referred to the upper body of an individual, including a thorax and an abdominal area. The thorax includes the chest, and the abdominal area includes the waist. The method further includes the step of sliding the slider along the trunk belt so that the drainage bag is in a desired position and/or adjusting the effective length of the supports strap using the position adjuster.

Also included are kits that are usable by an individual who has a condition in which body fluids are drained. The kit includes a drainage bag and a drainage bag support apparatus. The drainage bag support apparatus includes one or more trunk belts, one or more sliders, one or more support straps, and one or more retention devices, as described herein. The trunk belt can also have a fastener that would allow the trunk belt to be securely worn around the trunk of an individual.

Advantages of the present invention include the ability to attach the apparatus to various locations around the trunk of an individual. While it may be sufficient to have the apparatus attach to only the waist for a specific use, such as that of a Foley catheter, in an embodiment, it is necessary to be able to attach the support apparatus to other locations in the abdomen or thorax for other medical conditions. Limitations requiring attachment only to the waist area are likely to be prohibitive for the use of the apparatus for medical conditions which require the drainage bag to be placed near or higher than the abdominal area, or for medical conditions that specifically require no belt or other clothing be worn around the abdominal area. Another advantage of the present invention is the ability to attach more than one bag to the apparatus. It is beneficial to be able to carry multiple bags, for example when it is challenging for the patient to exchange filled bags with new ones, when circumstances such as the social environment make it difficult to change bags, when a patient desires the safety of an extra bag, or when the underlying conditions require use of multiple bags. An additional advantage of the present invention is the ability to carry multiple bags in multiple ways. For instance, the present invention allows one to stack multiple bags at a common area by attaching them to the same retention device. The present invention also allows one to carry multiple bags at different locations around the human body by attaching the bags to different retention devices supported by different support straps. Additionally, the present invention allows one to carry multiple bags by attaching some of them to the same retention device and some of them to a different retention device or to different retention devices. A further advantage of the present invention is the freedom it allows in placement and movement of the drainage bags during daily activities such as changing, using the bathroom, etc. Other advantages of the present invention include the ability to adjust the length of the trunk belt, the ability to adjust and lock the length of the support strap or support straps, and the ability to quickly and easily release and reattach the drainage bags.

BRIEF DESCRIPTION OF THE DRAWINGS

The foregoing and other objects, features, and advantages of the invention will be apparent from the following more particular description of preferred embodiments of the invention, as illustrated in the accompanying drawings in which parts are referred to by reference characters across different views. The drawings are not necessarily to scale, emphasis instead being placed on illustrating the principles of the invention. Sizes and relative proportions of the illustrated components can be changed without departing from the scope of the claimed invention.

DETAILED DESCRIPTION OF THE INVENTION

A description of preferred embodiments of the invention follows.

The present invention relates to an apparatus that can be used by individuals who have biological fluids being drained from their bodies due to a variety of medical conditions. The present invention pertains to a drainage bag support apparatus that allows individuals to carry drainage bags in a comfortable and efficient manner.

Figure 1:
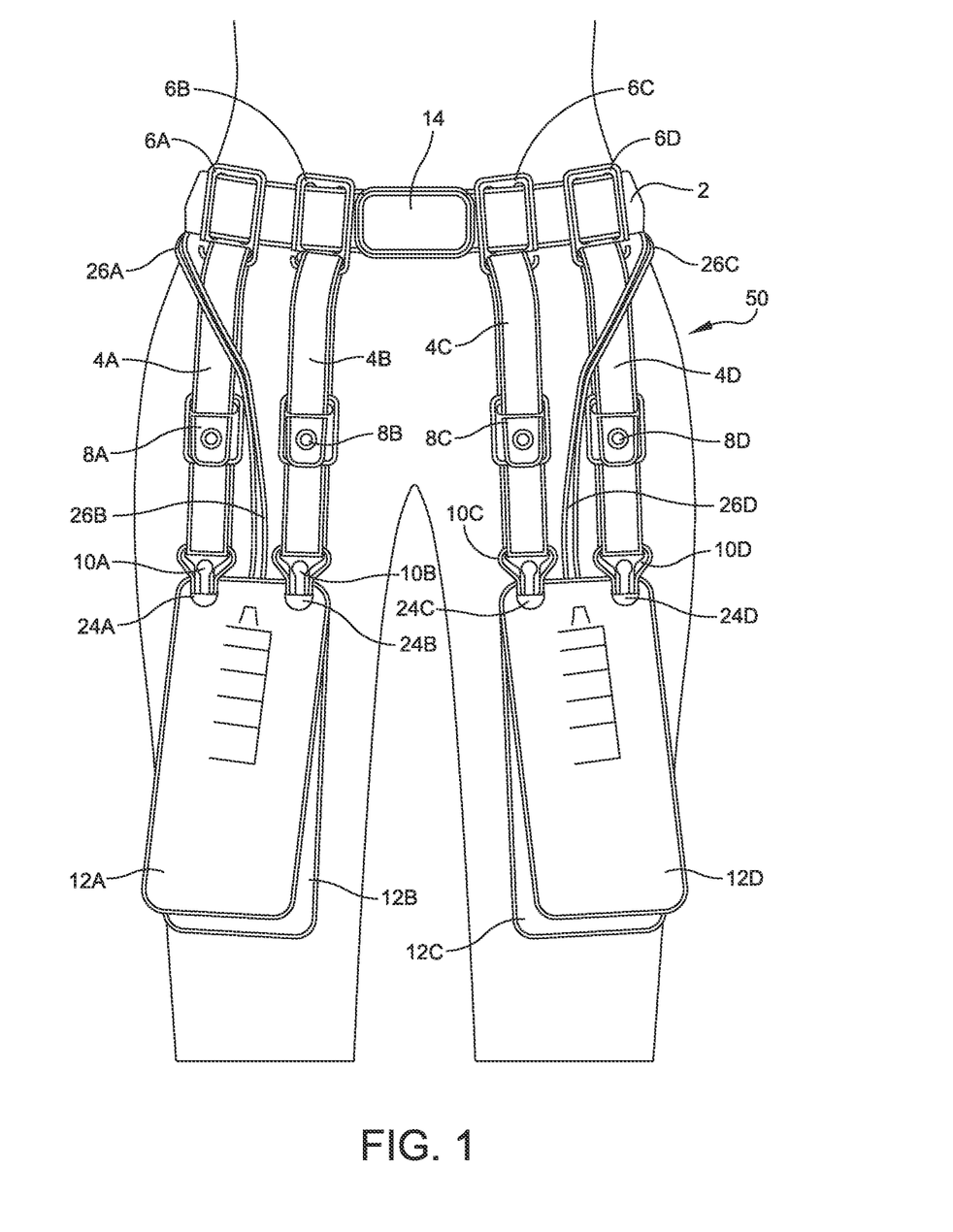
FIG. 1 is a schematic of a drainage bag support apparatus fitted around an individual.

Referring to FIG. 1, apparatus 50, also referred to as the drainage bag support apparatus 50, allows an individual to support one or more drainage bags. Thus, individuals using the apparatus can hold or carry drainage bags while being able to use their hands and while also being able to move around.

Medical conditions that use the drainage bag support apparatus of the present invention include abscesses at various locations such as abdominal abscesses, kidney conditions that require percutaneous nephrostomy, non-kidney conditions that require percutaneous nephrostomy, bladder conditions due to neurogenic causes (e.g., spinal cord injury, spina bifida, and multiple sclerosis), bladder problems due to non-neurogenic causes (e.g., infravesical obstruction due to prostate enlargement, urethral strictures and post-operative urinary retention), sedation or anesthetization prior to medical operations, being comatose, not being able to use a toilet due to physical injury or paralysis, kidney diseases that need monitoring of urine output, complications due to C-sections, needs arising during the induction of labor (childbirth), prostatic hypertrophy, congenital defects or traumatic disruption of the urinary tract, obstructions such as kidney stones, cancer, conditions requiring urostomy, pyonephrosis, hydronephrosis, infections of the urinary bladder, damages to the urethra, urinary retention, urinary incontinence, problems arising out of surgeries, and other health problems.

Such conditions require the use of catheters, which are tubes that can be inserted into a part of the body. Catheters can be used to perform a range of different functions, including drainage of biological fluids from the body. They can be inserted through the skin (percutaneous), into a body cavity, into a duct (such as the urethra), or into a body vessel (such as the arteries, veins, and the capillaries). After insertion, they can be left in for a brief time such as during an operation, for a prolonged time such as a full day, or even permanently. They can also be used intermittently. An example of a catheter is the Foley catheter, which is used to drain fluids from the urinary bladder into an outside drainage bag.

Figure 2:
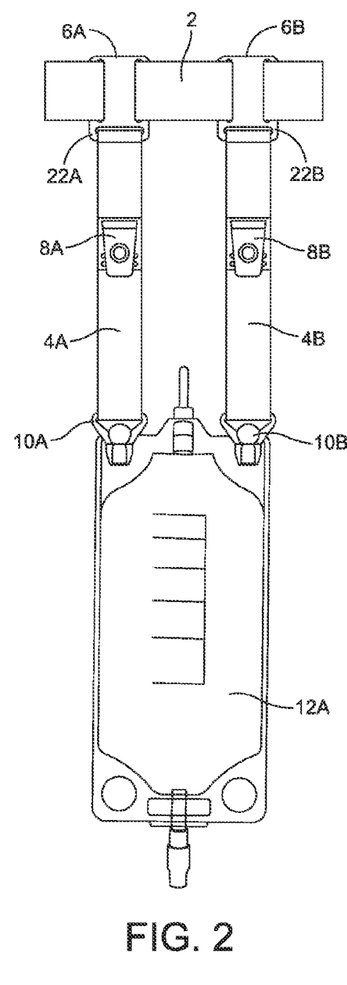
FIG. 2 is a schematic of exemplary components of a drainage bag support apparatus attached to a drainage bag. Shown components of the present invention include a trunk belt, two sliders, two support straps, two position adjusters, and two retention devices.
Figures 8A, 8B, 9, 10A, 10B, 10C, 10D:
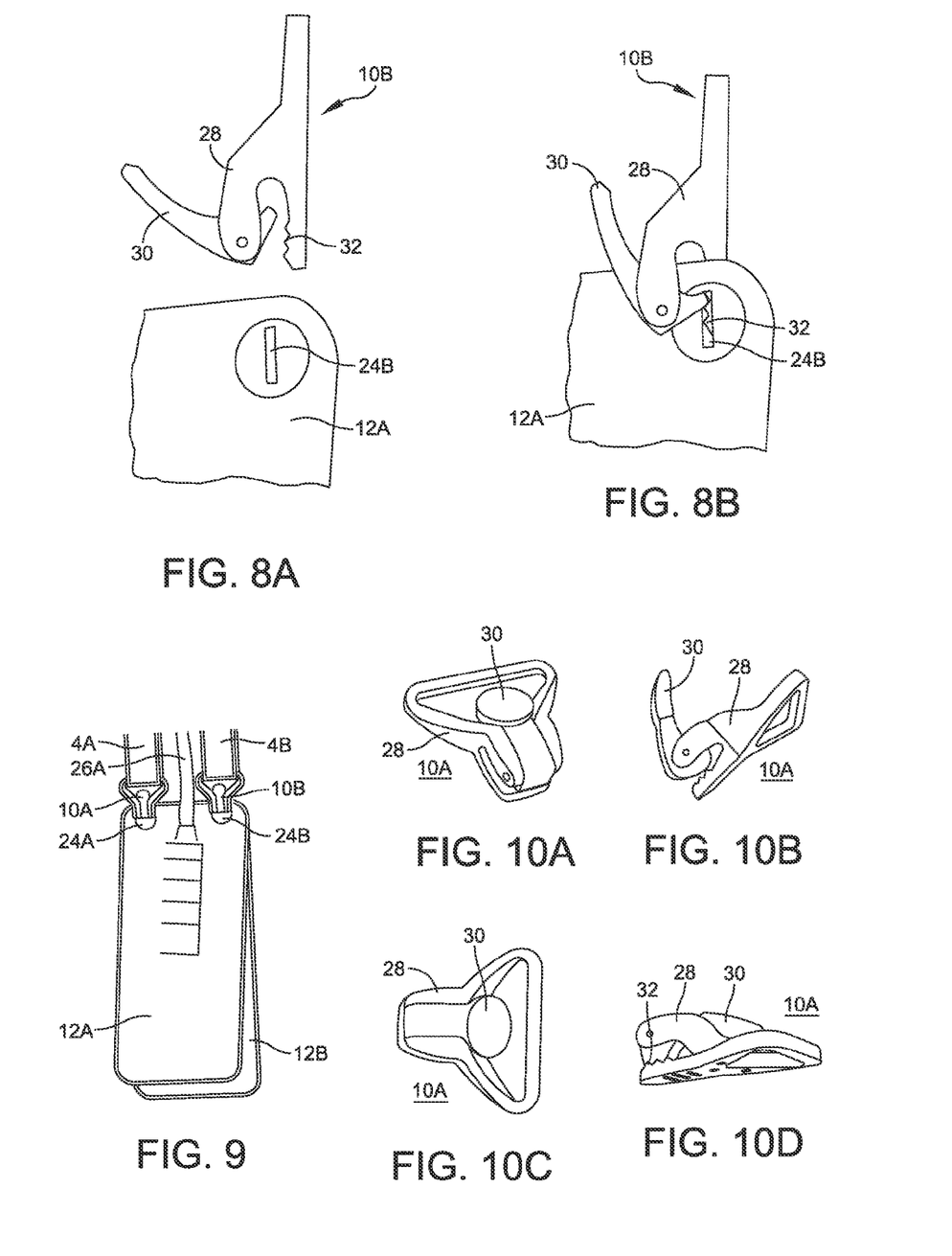
FIG. 8A is a schematic showing a detailed view of a retention device and a partial view of a drainage bag prior to being connected to one another. Also shown is an available bag opening to accommodate gripping parts of the retention device.
FIG. 8B is a schematic showing the retention device of FIG. 8A while gripping the drainage bag through the drainage bag opening.
FIG. 9 is a schematic showing a frontal view of two drainage bags each attached to both of two retention clips that are attached to two support straps (partial view). Catheter tubing (partial view) attached to drainage bag is also shown.
FIG. 10A is a schematic showing a perspective view of a quick release retention clip, which is an embodiment of the retention device that includes a retention device base and a retention device lever.
FIG. 10B is a schematic showing a side view of the quick release retention clip of FIG. 10A. Also shown are a retention device base, a retention device lever, and retention device teeth.
FIG. 10C is a schematic showing a top view of the quick release retention clip of FIG. 10A. Also shown are a retention device base and a retention device lever.
FIG. 10D is schematic showing a perspective side view of the quick release retention clip shown in FIG. 10A. Also shown are a retention device base, a retention device lever, and retention device teeth.

Exemplary drainage bags 12A-D are shown in FIG. 1. Various embodiments of drainage bags are known in the art, and some are depicted in FIGS. 1, 2, and 9, which can be used to collect the drained fluid. Such drainage bags are manufactured by companies such as C. R. Bard, Inc. (Murray Hill, N.J.), Kendall Healthcare (part of Covidien; Mansfield, Mass.), Medline Industries, Inc. (Mundelein, Ill.), and Rusch (part of Teleflex Incorporated; Limerick, Pa.). They range in sizes, some examples being 1500 ml (51 oz.), 2000 ml (68 oz.) and 4000 ml (136 oz.). Manufacturer's directions generally suggest that during use such bags be kept below the area from which fluids are drained so that gravity would help fluid move away from the body. Fluid from drainage bags that are not kept below the drainage site are at risk for a backflow of fluids flowing toward the drainage site.

Often it is necessary to change the drainage bags. For example, a user can empty the bag when it is filled partially or filled to full capacity. The same bag can be attached after it is emptied. In certain cases, to minimize the risk of infection, a new drainage bag can be used after the old one is removed. Different conditions require changing the drainage bags in different time intervals. In certain embodiments, it is preferable to use multiple drainage bags so one does not need to change the bags as often but rather simply use another bag already attached. Accordingly, embodiments of the present invention allow the user to support a single drainage bag, or two or more drainage bags in a number of configurations and/or positions.

As shown in FIG. 1, an embodiment of drainage bag support apparatus 50 includes four support straps (support straps 4A, 4B, 4C and 4D), four sliders (sliders 6A, 6B, 6C, and 6D) that connect each of the support straps (support strap 4A, 4B, 4C, and 4D) to trunk belt 2. Apparatus 50 includes retention devices 10A, 10B, 10C, and 10D slidably connected to support straps 4A, 4B, 4C, and 4C, respectively. In the embodiment shown in FIG. 1, each pair of drainage bags is attached to the same pair of retention devices (e.g., drainage bags 12A and 12B are attached to retention devices 10A and 10B and drainage bags 12C and 12D are attached to retention devices 10C and 10D). Also shown in FIG. 1 is fastener 14 that enables a user to secure trunk belt 2 around an area of an individual's trunk. In this embodiment, fastener 14 comprises a loop part (14A) and a hook part (14B).

By trunk, it is referred to the human trunk, which includes the portions of human body that comprise the thorax and the abdomen. Since the abdomen includes the waist, the waist is also included as part of the trunk. Referring to FIGS. 1, 2, 3A, 5A, 5B, and 6, trunk belt 2 is secured around the trunk. In an embodiment, trunk belts include, for example, a harness, belt, loop, rope, band, a combination thereof, and the like. In an embodiment, the trunk belt can be made of elastic materials. Examples of elastic materials include elastane, materials branded as SPANDEX® fabric, materials branded as LYCRA® material, latex, elastic natural rubber, elastic synthetic rubber, nitrile rubber, silicone rubber, neoprene, combinations thereof, and the like.

The trunk belt 2 can be secured around the trunk of an individual. By securing it is meant that the trunk belt is placed at an area of the human trunk from which it generally will not as a whole move significantly up or down without the user desiring to move it. One way to achieve this is by fastening the trunk belt 2 securely around an area of the trunk so that it remains substantially stationary. In another aspect, the trunk belt can be stabilized with the use of suspension straps (not shown) that hang from an area around the shoulders to the trunk belt.

The trunk belt can vary in width and can be narrow or wide. In an embodiment, its width ranges between about 0.1" and about 4" (e.g., between 0.5" and 3", or between 1" and 2").

This ability to secure the trunk belt in a variety of different sections of human trunk has significant advantages in that it allows the drainage bag support apparatus of the present invention to be used as part of the management or treatment of a diverse range of medical conditions. For example, the apparatus of the present invention can be worn low around the waist for the drainage of fluids from kidneys, from abdominal abscesses, or it can be worn higher for drainage of fluids from other areas that require or benefit from the trunk belt not being worn around the abdominal area. Alternatively, the apparatus of the present invention can be worn at a higher position on the trunk, for example to reduce or accommodate the length of tubing 26A, 26B, 26C, or 26D (See FIG. 1 or 9) needed.

Figure 5A:
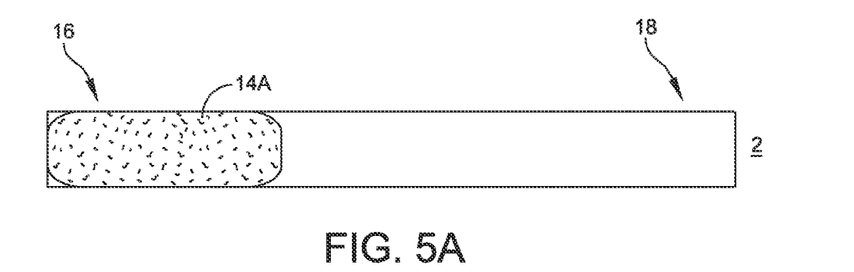
FIG. 5A is a schematic of a frontal view of a trunk belt having two ends, and a fastener part which is used to secure the trunk belt.
Figure 5B:
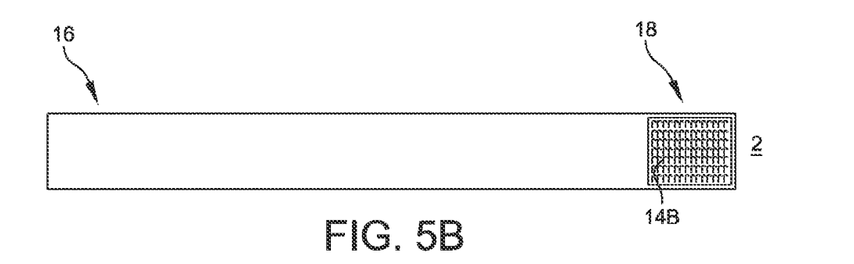
FIG. 5B is a schematic of a rear view of a trunk belt having two ends, and a fastener part that interacts with the other fastener part shown in FIG. 5A to secure the trunk belt.
Figure 6:
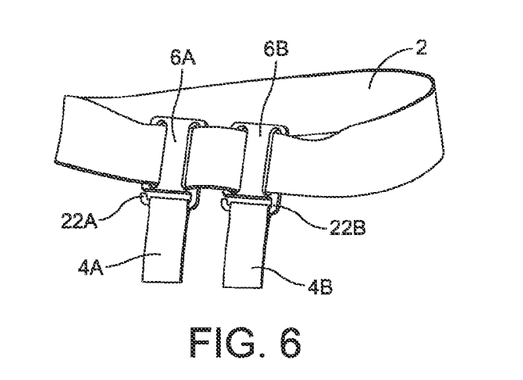
FIG. 6 is a schematic showing a perspective view of a trunk belt threaded through two sliders, displaying a partial view of two support straps.

Some embodiments of the present invention allow the adjustment of the effective length of the trunk belt. By the effective length of the trunk belt, or by the length of the trunk belt, it is referred to the length of the closed loop that the trunk belt 2 forms when it is secured around the trunk of an individual. Securing the trunk belt involves, in an aspect, fastening first end 16 (See FIG. 5A) of trunk belt 2 to second end 18 (See FIG. 5B) of the trunk belt 2. In another aspect, the trunk belt is fastened by attaching first end 16 of the trunk belt 2 to a portion of the trunk belt 2. Thus, even though the end to end length of a trunk belt 2 in its open form can be constant, the effective length of the trunk belt can be adjusted to fit the individual. In some embodiments, the trunk belt has no open form; it remains in a closed form, although it's effective length can be adjusted to secure it in place. A fastener can be used to secure the trunk belt and adjust the effective length of the trunk belt. FIGS. 1, 5A, and 5B show fastener 14 which is a hook and loop fastener. In an embodiment, the fastener can be any securing means, such as a strap, snap, series of snaps, buckle, cam buckle, center release buckle, button, series of buttons, rivet, hook, series of hooks, elastic member, position adjuster, key-lock arrangement, tie, lace, clip, series of clips, zipper, metal loop, roller loop, drawstring-and-cord lock arrangement, hook-to-hook arrangement, hook-and-loop arrangement, bungee cord-and-cord lock arrangement, block and tackle arrangement, rope and hook arrangement, chord and hook arrangement, snap hook, trap-lock, plastic trap-lock, magnet, slide, plastic slide, adhesive, and multiples, combinations, and the like thereof. One embodiment uses a hook tab fastener, which can be plastic and can be hot welded to the belt or glued to the belt (e.g., using an adhesive). Fasteners known or developed in the future can be used so long as they allow the trunk belt to be secured to fit one or more areas of the user's trunk.

Figure 3A:
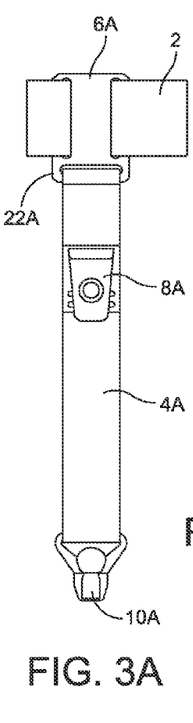
FIG. 3A is a schematic showing a frontal view of an embodiment of the apparatus of the present invention. In particular, the schematic shows a support strap attached to a trunk belt with a slider. The schematic also shows a support strap connected to a retention device to which a drainage bag (not shown) attaches and a position adjuster with which the effective length of the support strap is adjusted.

Referring to FIG. 1, 2, 3A, 3C, 6 or 7, a component that connects trunk belt 2 to support straps 4A, 4B, 4C or 4D is slider 6A, 6B, 6C or 6D, respectively. The slider can be any device that attaches the support strap to the trunk belt at various locations along the trunk belt. In particular, sliders are devices that can move or slide along the trunk belt in one or both directions. An exemplary device is a tri-point slider, which has two openings through which to thread the belt and a means for receiving the support strap (e.g., a hook). FIG. 7A shows a frontal view of tri-point slider 6A, whereas FIG. 7B shows a frontal view of tri-point slider 6B. FIGS. 2 and 3A show the slider through which the trunk belt has been threaded. Sliders for use with the present invention include those with a single opening, or a slider with more than two openings, as long as the slider has at least one opening through which the trunk belt can be threaded. FIG. 7A shows a total of two such slider openings (slider openings 20A1 and 20A2). Similarly, FIG. 7B shows slider openings 20B1 and 20B2. In some embodiments, the sliders have a mechanism that allows them to be locked in position along the belt. In other embodiments, the sliders are moved by detaching and then reattaching them, as opposed to continuously sliding them. An alternative way to achieve repositioning of the sliders in some embodiments is to have/keep fixed sliders and rotate the trunk belt.

The slider of the present invention, in an aspect, can have a side to side distance of between about 0.5" and about 4" (e.g., between about 1" and about 3", or about 1.5" and about 2.5"). By side to side distance it is referred to the distance between the sides of the slider that are relatively on the left and right sides of the individual when the slider is secured along the trunk belt. The slider of the present invention can also, in another aspect, have a top to bottom distance of between about 0.1" and about 4" (e.g., between about 0.5" and about 3", or between about 1" and about 2"). Any size slider can be used with the present invention as long as it slides along, or attaches to, or can be repositioned along the trunk belt as described herein.

By sliding, it is referred to a slider moving along the length of the trunk belt in either direction or both directions. Such a movement involves the user exerting force in the direction the slider should slide. In other words, the user exerts force to overcome friction between the slider and the belt to allow it to move. When worn by an individual, the range of the movement can be minimal (e.g., less than 5% of the effective length of the belt) or maximal wherein the maximum amount is limited by the effective length of the belt trunk.

Figure 7A:
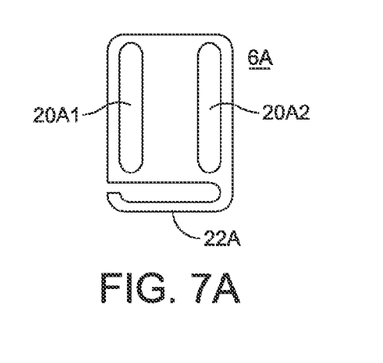
FIG. 7A is a schematic showing a frontal view of a tri-point slider, which is an embodiment of the slider.
Figure 7B:
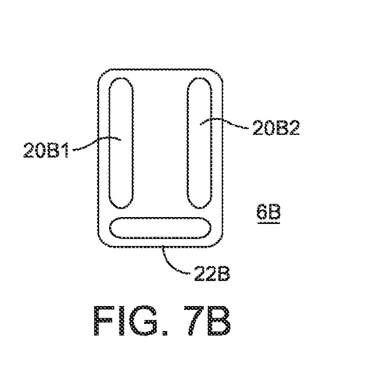
FIG. 7B is a schematic showing a frontal view of a tri-point slider with a closed hook portion, the tri-point slider being an embodiment of the slider.

In an embodiment, the sliders used in the present invention include a means for receiving the support strap. As shown in FIGS. 2, 3A, 7A, and 7B, hook 22A receives support strap 4A. Other means for receiving the support strap include an opening, loop, fastener, snap, clip, retention device, combinations thereof, and the like. In an aspect, the sliders can be made of any solid material, including metals, wood, glass, ceramics, polymers, fabrics, plastics, combinations thereof, and the like. In one embodiment, the hook has an open edge, such as the one shown in FIG. 7A for hook 22A. In another embodiment, the hook can be closed, essentially becoming a bottom opening of the slider (FIG. 7B, opening 22B). For such an embodiment, the support strap can be threaded through the closed-hook/bottom-opening and used in a similar fashion to the support strap as described herein. In an embodiment, the slider can be an inherent area of the support strap, which would effectively loop around or through the trunk belt.

Referring to FIGS. 1, 2, 3A, 3B, 3C, 6, and 9, trunk belt 2, using slider 6A, is connected to support strap 4A. Examples of support straps include a strap, suspension strap, band, loop, chain, coil, wire, hank, restraint, tie, net, a combination thereof, and the likes. The support strap of the present invention can be made, in an aspect, of non-elastic materials, such as non-elastic nylon, or other non-elastic plastics. Other non-elastic materials used to make the support strap include non-elastic plastic, cured plastic, polyurethane, polyurethane coated nylon, modal, acetate, polyethylene, polyethylene with alternative molecular weights, lyocell, acrylic, polyolefin, glass fiber, carbon fiber, cardboard, cotton, fleece, terry cloth, leather, artificial leather; textile/fabric, rayon, nylon, synthetic fibers branded as KEVLAR® material, canvas, vinyl, material branded as CORDURA® material, polyester, material branded as TYVEK® material, material branded as TWARON® material, down, polypropylene, polypropylene and copolymers, or laminations of acrylic; a polyamide, an aramid, para-aramid synthetic fiber, polyester or epoxy resins layered with nylons, carbon braids, or fiberglass cloths; wool, yarn, sheepskin, a synthetic material, and combinations and the likes thereof. The same set of materials, in various embodiments, can also be used for the drainage belt. The material can be any material known or later developed so long as it is suitable for the use intended as described herein.

Figures 3B, 3C:
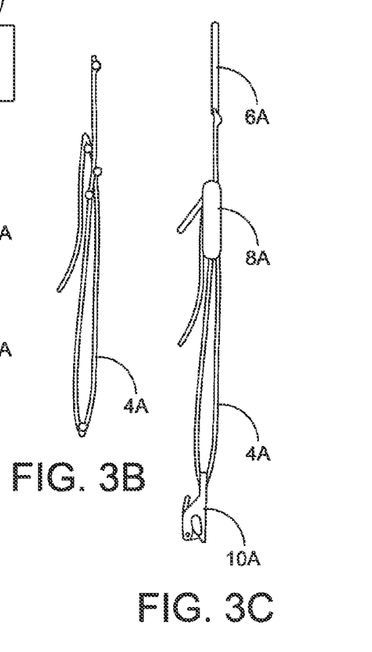
FIG. 3B is a schematic showing a side, cross-sectional view of the apparatus of FIG. 3A showing some pressure spots of a support strap threaded through a slider, a position adjuster, and a retention device.
FIG. 3C is a schematic depicting a side view of a support strap, slider, position adjuster, and retention device.
Figure 4:
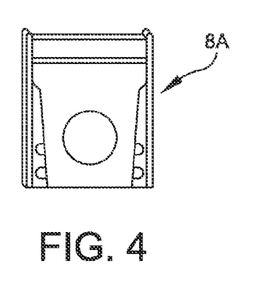
FIG. 4 is a schematic showing the frontal view of a cam buckle, which is an embodiment of the position adjuster.

Referring to FIGS. 1, 2, 3A, 3B, 3C and 4, the length of the support strap can be adjusted. By the length of the support strap, it is referred to the effective length of the support strap, which is the distance between the point at which the support strap connects to the slider and the point at which the support strap connects to the retention device. Adjustments to the length of the support strap can be made with a position adjuster. Position adjuster 8A is shown in the figures as a cam buckle (See FIG. 4). As used with the present invention, the position adjuster can be any number of devices such as a fastener, hook and loop fastener, strap, snap, series of snaps, buckle, cam buckle, center release buckle, button, series of buttons, hook, series of hooks, rivet, elastic member, key-lock arrangement, hook-to-hook arrangement, hook-and-loop arrangement, snap hook, elastic member, trap-lock, plastic trap-lock, tie, lace, clip, series of clips, zipper, metal loop, roller loop, drawstring-and-cord lock arrangement, bungee cord-and-cord lock arrangement, block and tackle arrangement, rope and hook arrangement, chord and hook arrangement, magnet, slide, plastic slide, adhesive, any combination thereof, and the like. Position adjusters known or developed in the future can be used as long as they allow an adjustment of a length of the part. FIG. 4 shows a cam buckle, which is an embodiment of a position adjuster 8A. FIG. 3B is a cross-sectional view showing the arrangement of three areas of contact between position adjuster 8A and the support strap 4A. As seen, in this embodiment, the support strap is threaded through in a pulley-like fashion between the sections of the slider with a member that locks the effective length of the strap into place.

By locking, it is meant that the length of the support strap does not change more than a certain percentage length during a period of use. In an embodiment, locked refers to a percentage change in the length of the support strap that is less than about 5%, about 2%, or about 1% during a period of about 1 hour, about 2 hours, about 5 hours, or about 24 hours. For example, the effective length of the support strap in a locked position, in an embodiment, can change by less than 5% within a period of about 2 hours; in another embodiment, the effective length of the support strap in a locked position can change by less than 5% of its initial length within a period of about 5 hours. While it is preferable to have no perceptible change in the effective length of the support strap, it is acceptable for some change to occur as long as the overall position of the drainage bag is maintained around the same location of the body.

There are many advantages of adjusting the length of the trunk belt, adjusting and locking the length of the support straps, and repositioning the sliders. Adjusting the length of the trunk belt allows different individuals who have different trunk perimeters to be able to fit the trunk belt to their trunk. Adjusting the length of the support strap allows placement of the drainage bags at different and more convenient locations around the human body. Whether the individual is in a hospital setting, in another specialized setting restricting mobility (e.g., where the individual is tied to a machine, support, or a bed), or in a social environment (e.g., where it is especially undesirable to leave the bags visible), the drainage bags can be positioned to suit the specific needs of the situation. In cases where different clothing choices allow for different ways of concealing the drainage bags, it is beneficial to adjust the length of the support straps and then move the drainage bags to a different area of the body. The ability to slide the sliders also bestows advantages as the length adjustability of the support straps do. Sliders allow individuals to place drainage bags at different places around their bodies.

With respect to FIGS. 1, 2, 3A, 3C, 8A, 8B, 9, 10A, 10B, 10C, and 10D, retention devices 10A, 10B, 10C and 10D allow for the attachment of drainage bags 12A-D to the support strap. As shown, one or more bags can be attached to one retention device, which in turn can be attached to at least one support strap. Retention devices connect and disconnect drainage bags. Retention device that can be used with the present invention includes e.g., a clip, quick release clip, hook, attachment device, fastener, snap, hook and loop fastener, any combination thereof, and the like. FIGS. 10A-D show four different views of retention device 10A. In the example shown, the quick release clips have a retention device base 28 that defines an opening to receive the drainage bags, a retention device lever 30 that moves and allows connection and disconnection of drainage bags, and retention device tooth or teeth 32 that engage the retention device lever 30 to secure it in a closed position to prevent the removal of the drainage bags. One way of attaching the drainage bag to the retention device is by placing part of the retention device through the bag opening (e.g., bag opening 24B of drainage bag 12A) and then moving the retention device to the closed position. In some embodiments, the retention device can be closed by engaging the retention device lever 30 with the retention device teeth 32.

In an embodiment, it is advantageous to be able to attach multiple drainage bags, to be able to swap or connect and disconnect drainage bags, and to be able to move the drainage bags during use. For an individual, it may not always be convenient to change a drainage bag for a new one or to remove a drainage bag, empty it, and reconnect it. Either time or space restriction can make such a swapping or changing difficult. Therefore, the ability of the present invention to allow attachment of more than one drainage bag makes the lifestyles of individuals with such needs less challenging. The solutions of the problems relating to the positions and numbers of drainage bags are among those solved by the present invention. Another solution embodied by the present invention is the capability to accommodate different drainage bags by the same drainage bag support apparatus. For example, for a typical bag having two bag openings, an individual can use two retention devices attached to two support straps and then adjust both the vertical length of the support straps and the horizontal distance between the support straps. Being able to adjust the horizontal distance between the support straps enables a user to properly place the two retention devices in relation to the two bag openings, thus making it possible to use the same drainage bag support apparatus with not only different drainage bags but also with different types of drainage bags (e.g., bags that might have a non-standard placement of bag openings, those that have fewer or more openings than two, or bags that have an alternative or new standard for the placement of the bag openings).

The materials that can be used to manufacture fasteners, sliders, position adjusters, and retention devices include metals, alloys, plastics (e.g., acetals, amino plastics, cellulosics, phenolics, etc.), ceramics, and composite materials. The materials used for each of fasteners, sliders, position adjusters, and retention devices can be the same as or different from each other. Some particular examples of materials for fasteners, sliders, position adjusters, and retention devices include polypropylene, polyurethane, as well as a variety of other plastics having suitable properties (e.g., hardness, durability, lack of irritation to human body). For persons having specific allergies (e.g., nylon), embodiments with materials different from those causing problems can be manufactured.

The materials for the support strap and the drainage belt can be the same as each other, except that certain materials that can be used for the belt, such as elastic ones, are not among the most preferred ones for the support strap. Both the belt and the strap can be made from nylon or polyester (e.g., polyethylene terephthalate) materials. For any of the components, materials now known or developed in the future can be used and substituted for each other or used together with each other. Some examples of materials that the strap and the belt can be made of include fabrics, textiles, cloth, webbing, wool, cotton, flax, polypropylene, polyester, DYNEEMA®, KEVLAR®, and TWARON®.

The drainage bag support apparatus can be manufactured and presented to the user in a variety of ways. For example, some components can be manufactured as unified components, instead of being separate ones. This would result in fewer number of items that constitute the apparatus. Some examples of this are a single piece slider-strap combination, strap-retention device combination, strap-adjuster combination, slider-strap-retention device combination, slider-strap-adjuster combination, and slider-strap-adjuster-retention device combination. One way such combined elements can be obtained is through molding more than one piece into a single piece or fusing multiple pieces in different ways (e.g., using adhesives, stitching, gluing together). The items of the drainage bag support apparatus can be pre-assembled (e.g., by the manufacturer, the distributer) or may be needed to be assembled by the end user (e.g., a patient, or a medical care professional). The sizes and relative proportions of any of the components can be changed without departing from the spirit of the claimed invention.

Various components (e.g., belt, support strap, slider, fastener, adjuster, retention clip) of the drainage bag support apparatus can be obtained from commercial sources, such as 3M Corporation (St. Paul, Minn.); National Webbing Products Co. (Plainview, N.Y.); National Molding Corporation (Miami Lakes, Fla.); Polartec, LLC (Lawrence, Mass.); Fabric Line (Portland, Oreg.), and Sonolite Plastics Corporation (Gloucester, Mass.).

The present invention further includes methods of using a drainage bag support apparatus 50. The steps of the method include a user (e.g., a health care professional) securing the trunk belt around the trunk of an individual, and then securing one or more drainage bags to the retention device. In one aspect, the drainage bag or bags are connected to a support strap with the retention device, and the support strap is connected to the trunk belt with the slider. In another aspect, the method includes adjusting the length of the trunk belt using the trunk belt fastener, and adjusting the effective length of the support strap using the position adjuster. Alternative embodiments include using any combination of the components described herein.

Additional embodiments of the present invention include kits that have one or more drainage bags and combinations of one or more of the components (e.g., trunk belt, support strap, fasteners, sliders, position adjusters and retention clips) of the drainage bag support apparatus. In one embodiment, the drainage bag support apparatus has one trunk belt, two support straps, two quick release bag clips, two tri-point sliders, and two cam buckles. In another embodiment, there is one trunk belt and the number of the support straps, sliders, position adjusters, and retention clips is equal to one another (e.g., two of each, three of each, four of each, etc.). The drainage bag support apparatus includes any of the embodiments described herein. The kit can also include, for example, additional catheters, tubing, tools to connect such components together, instruction manuals, other instruction materials such as videos, and the like.

EXEMPLIFICATION

The apparatus of the claimed invention is the result of extensive knowledge and experience with preexisting devices and their shortcomings.

The present invention as shown in the figures was made. Specifically, the components were assembled as shown. The support strap was threaded through the retention clip and position adjuster. The sliders were threaded through the trunk belt through the slider openings. The support strap was then attached to the hook of the slider to thereby assemble the apparatus.

The main belt was made of elastic material and had a tab at the end that was made from a VELCRO® material. Other similar fastening material can also be used. This tab, in some prototypes was thermally welded, whereas in others, it was sewn in place. In one prototype, up to four tri-point sliders were used, which can be made of plastic resins and served as anchors for the suspension straps to attach. The suspension straps, in some prototypes, were made of nylon, whereas in another, they were made of polyester. The length of a strap was adjusted by the use of a clamp-like device, which was made of similar plastic resins as the tri-point sliders. Another component that can be similarly made of plastic resins was the suspension clip, a number of which can be used as part of the apparatus. The suspension clips were positioned at the distal end of the suspension straps.

Experiments were conducted at a medical office by testing different prototypes embodying the present invention. This allowed for the meeting of clinical challenges to the satisfaction of the patient and the physician. The tests involved changing various settings of the belt, such as its location along the thorax including the waist line, the suspension straps, such as their length, and the drainage bags, such as their number and volume. Multiple parts were made to coherently work together, and suitable materials include elastic materials (e.g., for the belt), polyester, nylon, polypropylene, and other plastics.

The relevant teachings of all the references, patents, and patent applications cited in this application are incorporated herein by reference in their entirety.

While this invention has been particularly shown and described with references to preferred embodiments thereof, it will be understood by those skilled in the art that various changes in form and details may be made therein without departing from the scope of the invention encompassed by the appended claims.

What is claimed is:

1. A drainage bag support apparatus for use by an individual having a medical condition in which fluid is drained, wherein the drainage bag support apparatus comprises:
    (a) an elastic trunk belt having a fastener to secure the trunk belt around a trunk of the individual; wherein the trunk belt has a first end and a second end, and wherein the fastener attaches the first end to the second end, the first end to a portion of the trunk belt, the second end to a portion of the trunk belt, or a portion of the trunk belt to another portion of the trunk belt
    (b) at least two pairs of sliders, wherein each slider is slidably and reversibly attached to the trunk belt;
    (c) at least two pairs of non-elastic support straps, wherein each support strap is reversibly attached at an upper portion to one of the sliders attachable to the elastic trunk belt and wherein each support strap comprises a position adjuster that is configured to independently adjust the length of the support strap from the upper portion to a lower portion and to lock the length of the support strap from the upper portion to the lower portion, wherein each support strap position adjuster is configured to lock the length of the support strap such that the change in length of the locked support strap remains within 10 percent of a lock-in effective distance for a period of at least 24 hours following the locking of the support strap; and
    (d) at least two pair of retention devices provided as cam buckles, each retention device of each pair of retention devices configured to attach to the lower portion of one of each pair of the support straps, each pair of retention devices configured for receiving at least two drainage bags; each drainage bag having two or more pairs of bag openings, each pair of openings configured to attach to each pair of retention devices, wherein each retention device is configured to reversibly attach to one of the drainage bag openings and wherein each drainage bag can be attached or removed from each pair of retention devices independently of each other drainage bag;

wherein a combination of the non-elastic support straps, elastic trunk belt; fasteners, position adjuster, and sliders are configured to be attached to each other and adjusted and locked in length and position via the position adjusters, such that the drainage bags can be attached, secured, positioned, adjusted, and removed in less time than drainage bag systems without the combination; and wherein the combination is configured for: adjusting the drainage support apparatus to reduce visability of the baggage support apparatus under clothing; and attaching, securing, positioning, adjusting, and removing the bags at different locations around a body of the individual in different environments including a hospital setting, a restricted mobility setting, a social environment, and different clothing environments.

2. The apparatus of claim 1, wherein the slider has a means for receiving the support strap.

3. A method of using a drainage bag support apparatus by an individual having a trunk and having a medical condition in which fluid is drained into a drainage bag, the method comprising the steps of:
    providing a drainage bag apparatus comprising:
    (a) an elastic trunk belt having a fastener to secure the trunk belt around a trunk of the individual; wherein the trunk belt has a first end and a second end, and wherein the fastener attaches the first end to the second end, the first end to a portion of the trunk belt, the second end to a portion of the trunk belt, or a portion of the trunk belt to another portion of the trunk belt
    (b) at least two pairs of sliders, wherein each slider is slidably and reversibly attached to the trunk belt;
    (c) at least two pairs of non-elastic support straps, wherein each support strap is reversibly attached at an upper portion to one of the sliders attachable to the elastic trunk belt and wherein each support strap comprises a position adjuster that is configured to independently adjust the length of the support strap from the upper portion to a lower portion and to lock the length of the support strap from the upper portion to the lower portion, wherein each support strap position adjuster is configured to lock the length of the support strap such that the change in length of the locked support strap remains within 10 percent of a lock-in effective distance for a period of at least 24 hours following the locking of the support strap; and
    (d) at least two pair of retention devices provided as cam buckles, each retention device of each pair of retention devices configured to attach to the lower portion of one of each pair of the support straps, each pair of retention devices configured for receiving at least two drainage bags; each drainage bag having two or more pairs of bag openings, each pair of openings configured to attach to each pair of retention devices, wherein each retention device is configured to reversibly attach to one of the drainage bag openings and wherein each drainage bag can be attached or removed from each pair of retention devices independently of each other drainage bag
    (e) securing the elastic trunk belt around the trunk of the individual via the fastener; and
    (f) attaching, securing, positioning, adjusting, and removing at least one of the at least one pair of drainage bags used by the individual with the drainage bag support apparatus, such that the non-elastic support straps, elastic trunk belt; fasteners, position adjuster, and sliders, attach to each other and are adjustable and lockable in length and position via the position adjusters, such that the drainage bags are attached, secured, positioned, adjusted, and removed in less time than drainage bag systems without non-elastic support straps, elastic trunk belt; fasteners, position adjuster, and sliders, the reduced time provided for increasing or reducing visability and the combination configured for attaching, securing, positioning, adjusting, and removing the bags at different locations around a body of the individual in different environments including a hospital setting, a restricted mobility setting, a social environment, and different clothing environments.

4. The method of claim 3, wherein the elastic trunk belt is be configured to be secured around the abdominal area or around the thorax of the individual.

5. A kit for use by an individual having a medical condition in which fluid is drained, the kit comprising:
(a) at least two drainage bags; and
(b) a drainage bag support apparatus, wherein the drainage bag support apparatus comprises:
   (i) an elastic trunk belt having a fastener to secure the trunk belt around a trunk of the individual; wherein the trunk belt has a first end and a second end, and wherein the fastener attaches the first end to the second end, the first end to a portion of the trunk belt, the second end to a portion of the trunk belt, or a portion of the trunk belt to another portion of the trunk belt;
   (ii) at least two pairs of sliders, wherein each slider is slidably and reversibly attached to the trunk belt;
   (iii) at least two pairs of non-elastic support straps, wherein each support strap is reversibly attached at an upper portion to one of the sliders attachable to the elastic trunk belt and wherein each support strap comprises a position adjuster that is configured to independently adjust the length of the support strap from the upper portion to a lower portion and to lock the length of the support strap from the upper portion to the lower portion, wherein each support strap position adjuster is configured to lock the length of the support strap such that the change in length of the locked support strap remains within 10 percent of a lock-in effective distance for a period of at least 24 hours following the locking of the support strap; and
   (iv) at least two pair of retention devices provided as cam buckles, each retention device of each pair of retention devices configured to attach to the lower portion of one of each pair of the support straps, each pair of retention devices configured for receiving at least two drainage bags; each drainage bag having two or more pairs of bag openings, each pair of openings configured to attach to each pair of retention devices, wherein each retention device is configured to reversibly attach to one of the drainage bag openings and wherein each drainage bag can be attached or removed from each pair of retention devices independently of each other drainage bag;

wherein a combination of the non-elastic support straps, elastic trunk belt; fasteners, position adjuster, and sliders are configured to be attached to each other and adjusted and locked in length and position via the position adjusters, such that the drainage bags can be attached, secured, positioned, adjusted, and removed in less time than drainage bag systems without the combination; and wherein the combination is configured for: adjusting the drainage support apparatus to reduce visability of the baggage support apparatus under clothing; and attaching, securing, positioning, adjusting, and removing the bags at different locations around a body of the individual in different environments including a hospital setting, a restricted mobility setting, a social environment, and different clothing environments.

* * * * *